(12) United States Patent
Bartic et al.

(10) Patent No.: US 8,423,143 B2
(45) Date of Patent: Apr. 16, 2013

(54) PROBE DEVICE FOR ELECTRICAL STIMULATION AND RECORDING OF THE ACTIVITY OF EXCITABLE CELLS

(75) Inventors: Carmen Bartic, Wilsele (BE); Bart Nuttin, Rotselaar (BE); Kris van Kuyck, Leuven (BE)

(73) Assignees: IMEC, Leuven (BE); Katholieke Universiteit Leuven (KUL), Leuven (BE)

( * ) Notice: Subject to any disclaimer, the term of this patent is extended or adjusted under 35 U.S.C. 154(b) by 1287 days.

(21) Appl. No.: 11/436,325

(22) Filed: May 18, 2006

(65) Prior Publication Data

US 2006/0265039 A1    Nov. 23, 2006

(30) Foreign Application Priority Data

May 20, 2005   (EP) ..................................... 05447117

(51) Int. Cl.
*A61N 1/34*   (2006.01)
(52) U.S. Cl.
USPC ................................................ 607/45; 607/2
(58) Field of Classification Search ................ 607/2, 45, 607/115–116; 600/377–379
See application file for complete search history.

(56) References Cited

U.S. PATENT DOCUMENTS

| 5,215,088 | A | | 6/1993 | Normann et al. | ............. 128/642 |
| 5,897,583 | A | * | 4/1999 | Meyer et al. | .................. 607/116 |
| 6,970,746 | B2 | * | 11/2005 | Eckmiller et al. | ............ 607/116 |
| 7,272,447 | B2 | * | 9/2007 | Stett et al. | ...................... 607/116 |
| 7,774,053 | B2 | * | 8/2010 | Garell et al. | ................... 600/544 |
| 2002/0022872 | A1 | | 2/2002 | Gielen et al. | .................. 607/116 |
| 2002/0082643 | A1 | * | 6/2002 | Milla et al. | ......................... 607/1 |
| 2002/0183817 | A1 | * | 12/2002 | Van Venrooij et al. | ........ 607/116 |
| 2003/0083724 | A1 | * | 5/2003 | Jog et al. | ........................ 607/122 |
| 2003/0181955 | A1 | | 9/2003 | Gielen et al. | .................... 607/45 |
| 2004/0155290 | A1 | * | 8/2004 | Mech et al. | ..................... 257/347 |
| 2004/0199235 | A1 | * | 10/2004 | Younis | .......................... 607/116 |

OTHER PUBLICATIONS

"Biomedical Microdevices for Neural Interfaces", Meyer et al. 1st Annual Internation IEEE-EMBS Special Topic Conference on Micro technologies in Medicine & Biology; Oct. 12-14, 2000, Lyon France.*
Motta et al., "Micromachined Probes for Deep Brain Stimulation," 2nd Annual International IEEE-EMBS Special Topic Conference on Microtechnologies in Medicine and Biology, May 2-4, 2002, Wisconsin, USA, Proceedings pp. 251-254.
Wise et al., "Wireless Implantable Microsystems: High-Density Electronic Interfaces to the Nervous System," proceedings of the IEEE, vol. 92, No. 1, p. 76-97, Jan. 2004.

(Continued)

*Primary Examiner* — Carl H Layno
*Assistant Examiner* — Paula J Stice
(74) *Attorney, Agent, or Firm* — McDonnell Boehnen Hulbert & Berghoff LLP (57) ABSTRACT

A probe device is described having a substrate and a die on top of the substrate. The die has an array of stimulation/recording sites having at least one stimulation means and at least one recording means. The substrate comprising the die is folded into a cylindrical shape or a shape with a conical cross-section and, therefore, limits damage when it is implanted in tissue to be examined or treated, e.g., the brain of a patient in case of a neuro-probe device for use in deep brain stimulation.

17 Claims, 5 Drawing Sheets

OTHER PUBLICATIONS

Malachowski et al., "Novel Thin Film Cuff Electrode for Neural Stimulation," 26th International Spring Seminar on Electronics Technology, May 8-11, 2003. IEEE.

Martinoia et al., "Development of ISFET Array-Based Microsystems for Bioelectrochemical Measurements of Cell Populations," Biosensors Bioelectronics 16 (2001) 1043-1050, XP-002269304.

Schneider et al., "Implantable Flexible Electrodes for Functional Electrical Stimulation," Medical Device Technology, Jan./Feb. 2004, XP-002344312.

European Search Report dated Sep. 9, 2005, EP 05 44 7117.

* cited by examiner

PROBE DEVICE FOR ELECTRICAL STIMULATION AND RECORDING OF THE ACTIVITY OF EXCITABLE CELLS

RELATED APPLICATIONS

The present patent application claims priority under 35 U.S.C. §119(b) to EP 054471.17.2, which was filed May 20, 2005. The full disclosure of EP 05447117.2 is incorporated herein by reference.

FIELD

The present invention provides a device allowing controlled 3D stimulation of excitable cells, such as specific deep brain nuclei, and simultaneous recording of the electrical activity of the stimulated cells and a method for the manufacturing of such a device. The device may be used in surgical Parkinson's Disease therapy, but is also suitable for neuromodulation in other disorders such as, for example, epilepsy and obsessive-compulsive disorders (e.g., depression, anorexia nervosa, etc.), for example in motor cortex stimulation or uro-abdominal functional stimulation.

BACKGROUND

Excitable cells in tissues (e.g., nervous, cardiac, or muscular tissue) can be modulated by electric fields, in that way providing a possible therapeutic approach for several disorders affecting these tissues. An example may be chronic deep brain stimulation (DBS), a treatment for symptoms of many disorders, such as movement disorders (e.g., essential tremor, posttraumatic tremor, tremor in multiple sclerosis, dystonia), epilepsy, chronic pain, etc. Taking the example of DBS for akinesia, i.e., the inability to start a movement, which is one of the symptoms of Parkinson's disease.

Figure 1:
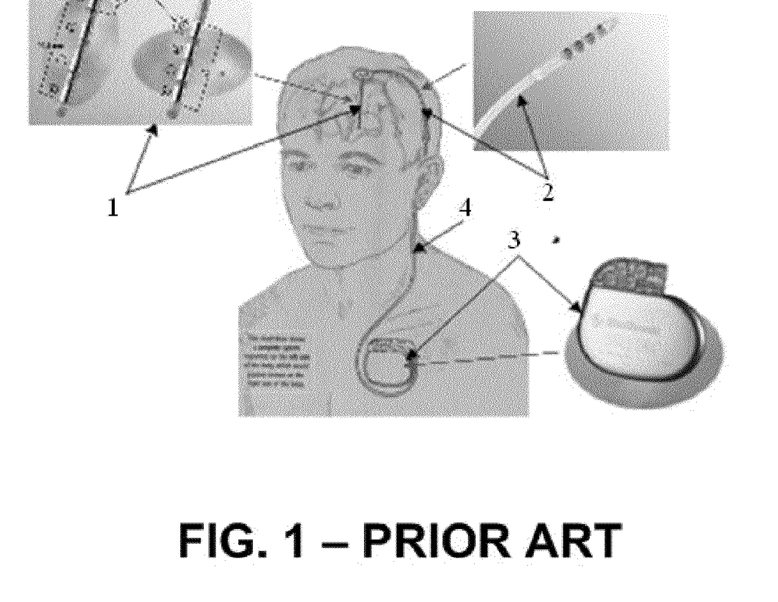
FIG. 1 is an illustration of a prior art multi-electrode lead implanted in the brain of a patient.

DBS comprises implantation of an electrode 1, which is preferably a multi-electrode, connected to a lead 2 into the subthalamic nucleus (STN), which is a co-ordinating motor center through which incoming nerve impulses are directed to appropriate parts of the globus pallidus. Furthermore, a pulse generator or stimulator 3 is required to which the lead 2 is connected through an extension wire 4 and which is surgically implanted under the skin, e.g., in the upper chest of a patient. This is illustrated in FIG. 1.

The extension wire 4 is threaded from the electrode lead 2 from the scalp area under the skin to the chest where it is connected to the pulse generator or stimulator 3. To turn it on and off, the patient passes a hand-held magnet over the pulse generator or stimulator 3. For example, the pulse generator or stimulator 3 may be turned off at night. In the on-position, the pulse generator or stimulator 3 produces a high-frequency, pulsed electric current that is sent along the electrode to the STN. The electrical stimulation in the STN takes away the akinesia. The stimulus parameters can be adjusted to provide the best response and minimize adverse reactions.

A disadvantage of the above-described system is that the pulse generator or stimulator 3 has to be replaced to change batteries, which, theoretically, should last 5 years. However, in practice, the batteries last much less. Sometimes they have to be replaced every year. This is unpleasant for the patient because a local incision at the stimulator location is required. Furthermore, it is expensive for the health care system.

Currently, in surgical practice, a medical device called the Activa® Tremor Control System, manufactured by Medtronics Inc., is used, which has a good success rate when compared to standard medications. Furthermore, a line of neurological pulse generators similar to Activa® has been produced by Medtronics Inc.

The Activa® Tremor Control System device provides electrical pulses to precisely targeted areas of the brain. It can be compared to a cardiac pacemaker. This system, which is fully implantable, consists of an insulated microwire (lead) terminated in 4 electrodes to be implanted in the STN, connected via an insulated wire with a pulse generator device placed underneath the skin in the chest or abdomen. This device generates the electrical pulses necessary for the stimulation. Although highly effective for the large majority of the Parkinson patients, clinical application of DBS (Activa® Therapy provided by Medtronic) shows a wide range of outcomes.

The device implantation is performed by a functional stereotactic neurosurgeon, that is, a neurosurgeon that specializes in treating central nervous system function disorders using stereotactic techniques. This means that a stereotactic head frame is used to keep the patient's head still during surgery and the neurosurgeon uses imaging techniques such as magnetic resonance imaging (MRI) or computed topography (CT) to map the brain and locate the position of the site to be stimulated (anatomic target).

An essential part of the implantation of the DBS electrode is the physiological test stimulation when the electrode is approaching the anatomical target. To verify the efficacy of the stimulation, the full cooperation of an awake patient is required. However in many cases, the cooperation with the patient is not sufficient to achieve optimally functional brain target and, therefore, microelectrode-based recordings of the cellular activity in and around the intended functional brain target can be used in order to overcome the need for the patient cooperation. Currently, a microelectrode recording procedure is used intra-operatively to identify the boundaries of the STN. This procedure makes use of five parallel microelectrode trajectories in a rectangular grid, which explores the brain structure in discrete steps of 0.5 mm.

To help the clinician place the DBS electrode and decide which stimulation sites to use, it could be valuable to define the anatomical location of each stimulation site relative to the target structure. This information is currently difficult to obtain because of the limited resolution of the imaging techniques as well as due to individual variations in the position of individual brain structures. Signal recording with high spatial resolution and high signal to noise ratio as well as signal analysis that would enable automatic recognition of the functional brain target would therefore enable the optimization and standardization of the therapy. Moreover, chronically implanted microelectrodes should provide an effective follow up procedure after the implantation, by actively enabling to adjust the stimulation parameters in order to adapt to possible movement of the implanted device in respect to the relevant brain structures.

Figure 2:
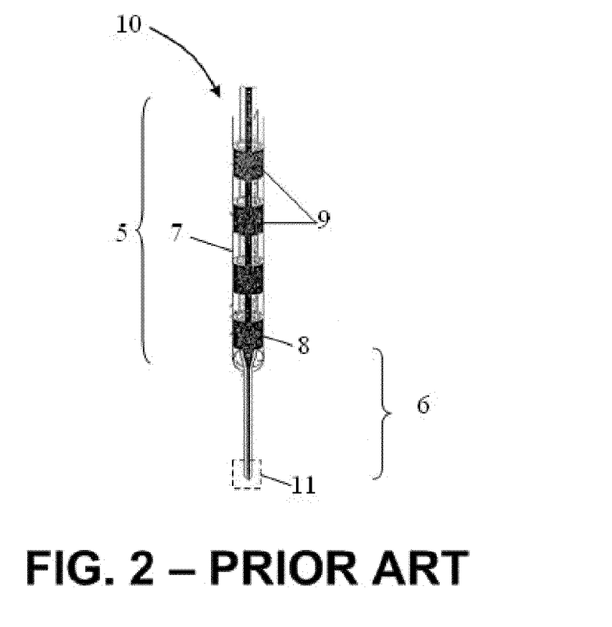
FIG. 2 is an illustration of a neuro-probe according to the prior art.

One of the systems of Medtronics Inc. is described in U.S. Patent Publication No. 2002/0022872. This document provides a lead for brain stimulation which is capable of micro single cell recording and macro test stimulation. Such lead is illustrated in FIG. 2. The lead 10 comprises a macro-segment 5 and a micro-segment 6; the macro-segment 5 having a length that is longer than the length of the micro-segment 6. The macro-segment 5 most preferably comprises a lead casing 7. A macro-electrode 8 is positioned at the distal end of the casing 7 and conductors 9. The micro-segment 6 most preferably comprises a micro-electrode 11 encapsulated within an insulating layer. The micro-electrode 11 has, at its exposed tip, an electrode surface area less than about 500 μm², and even more preferably an electrode surface area less than 1 µm² for single cell recording applications. In the device described in U.S. Patent Publication No. 2002/0022872, the macro-electrodes are used for stimulation, i.e., to deliver stimulation pulses, while the micro-electrode at the tip of the micro-segment is used for recording.

However, the system described in U.S. Patent Publication No. 2002/0022872 only has four positions from which to perform measurements (four macro-electrodes 8). This only makes it possible to measure in the length of the probe. Furthermore, the system cannot be used for chronic stimulation. Therefore, the system has to be removed and replaced by a conventional DBS lead.

Few groups in the world are attempting to use micromachining techniques in order to fabricate multi-site recording probes to be implemented in cortical prostheses.

Figure 3:
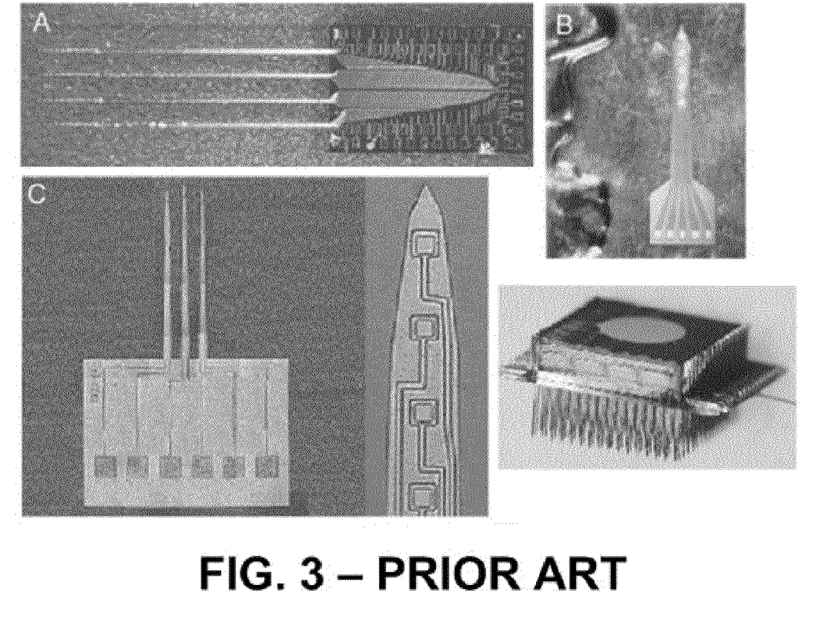
FIG. 3 shows examples of 2D (A-B-C) and 3D (D) multi-site needle probes according to the prior art.
Figure 4:
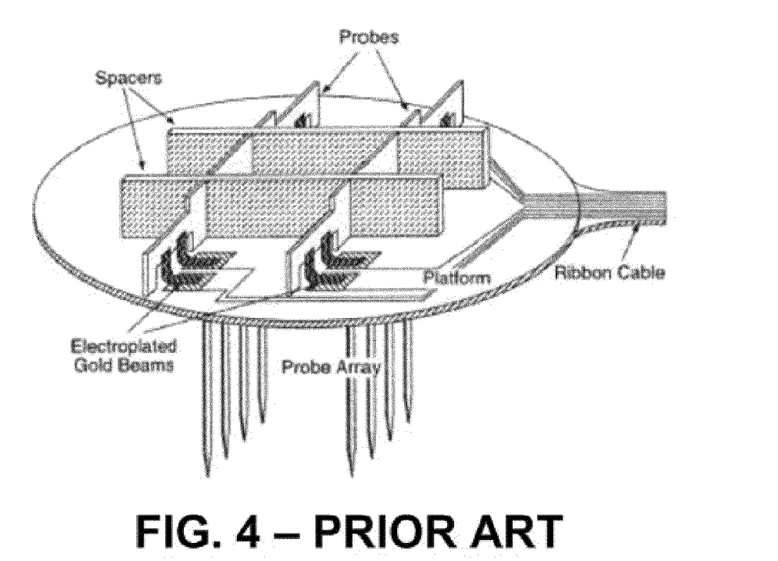
FIG. 4 illustrates a 3D assembly of a probe according to the prior art.

Michigan University has provided a probe, in the further description referred to as 'Michigan probe'. FIGS. 3A, 3B, and 3C illustrate examples of 2D needle probes, and FIG. 3D illustrates an example of a 3D multi-site needle probe. A Michigan probe comprises a plurality of needles and a large number of recording sites, formed by passive iridium electrodes placed along the shaft of each needle (see FIG. 3). This makes it possible to record electrical activity at different depths in the cortex. Designed for monkey recordings, the length of each needle in a probe is around 3.8 mm with the shank tips spaced at ~150 um. Readout electronics have been integrated at the probe terminal opposite to recording tip. The main challenge with the Michigan probe is represented by the creation of 3D arrays starting from 2D probes, namely the transfer of the 2D probes onto the supporting platform. This is currently done by micro-assembly as illustrated in FIG. 4.

Figure 5:
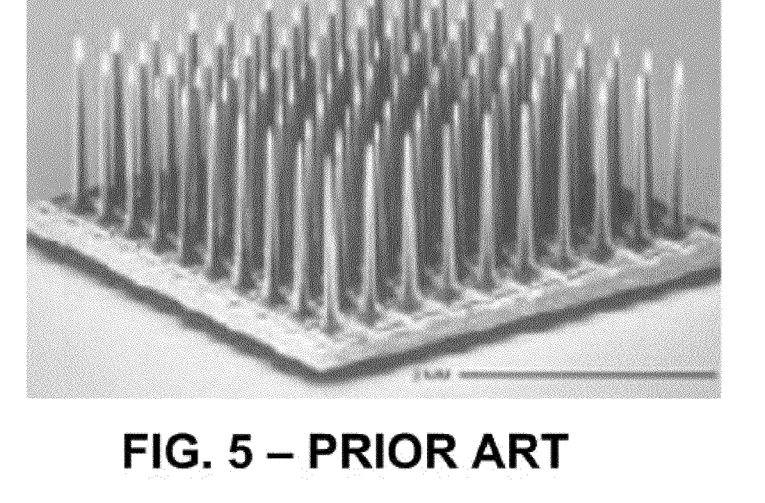
FIG. 5 illustrates a 3D micro-fabricated cortical probe according to the prior art.

A different approach is proposed by Utah University. Their 3D probe, further referred to as 'Utah probe' and illustrated in FIG. 5, consists of a 10×10 array of needles having a single recording site at the tip. With only one recording site at a fixed cortical depth, the Utah probe suffers from the same placement problems as microwires.

Motta, P. S. and Judy, J. W., have described a method for the fabrication of micromachined probes for deep-brain stimulation ("Micromachined probes for deep brain stimulation", 2nd Annual International IEEE-EMBS Special Topic Conference on Microtechnologies in Medicine and Biology", May 2-4, 2002, Wisconsin USA, Proceedings pp. 251-254). Their method makes use of the electroplating technique to create a probe with a microwire-like geometry with a tapering diameter. This probe comprises stimulation electrodes only, and no recording sites. It only allows depth modulation of the stimulation field and no 3D distribution.

The common problem with chronically implanted electrodes is that of the tissue-electrode interface. Any object inserted in the brain causes brain damage, disrupted blood vessels and microhemorrhage. Neurons are sliced or ripped as the electrode is inserted. Under these conditions glial cells begin to proliferate and form a loose encapsulation around the electrode at a considerable distance (100-200 µm). Chronically, this results in an increase of the electrode impedance, which leads to high electrical noise and poor quality recordings.

The size and the shape of the electrode and the way it is inserted are critical factors for the type of damage to be produced. All the prior art literature focuses on nail-like electrode shape, based on the assumption that small nail tip size will result in minimal tissue damage. However, the brain is continuously moving and in some cases when mechanical shocks may occur, these nails may act like micro-knives and section the blood vessels.

SUMMARY

A probe device which limits the damage in the tissue when it is inserted as well as a method of manufacturing and using the same is described. The probe can deliver stimulation pulses and perform measurements in three dimensions. Additionally, the probe device has sensing devices which enable high to low impedance conversion and, thus, enhance the signal to noise ratio of chronic recordings.

In a first aspect, the present invention provides a probe device for electrical stimulation and recording of activity of excitable cells present in tissue in which the probe device is implanted. For example, the probe device may be a neuro-probe device for electrically stimulating neurons present in brain tissue of a patient and for recording the activity of the neurons.

The probe device according to the first aspect of the invention comprises an array of pixels, wherein each pixel comprises at least one stimulation means and at least one recording means.

The recording means may be, for example, means that can be used for measuring, indicating, and/or reading the activity of excitable cells present in a tissue to be examined or treated. In one example, the tissue may be brain tissue, although the invention is not limited thereto.

In the probe device according to the first aspect of the invention, stimulation and recording means are positioned at a same site, forming a stimulation/recording site. Furthermore, because an array of stimulation/recording sites is present, it is possible to stimulate excitable cells and record activity of the stimulated excitable cells in at least two directions.

In embodiments of the invention the array of pixels may be located on a die. The die may, for example, be a semiconductor die, such as a silicon die. In other embodiments, however, the die may be a GaAs die or a SOI (silicon on insulator) die.

According to embodiments of the invention, the die may be positioned on a substrate. The substrate preferably is from biocompatible material, and may for example comprise one of parylene C, parylene N, polyimide, polysiloxane rubber, teflon, a noble metal, titanium, an oxide, $Si_3N_4$, or a biocompatible epoxy. The substrate may be shaped so as to enable, when introduced into tissue of a patient, 3D stimulation of excitable cells present in the tissue and 3D measurement of activity of the excited cells in the tissue. The tissue may, for example, be nervous, cardiac or muscular tissue.

According to embodiments of the invention, the substrate may have a first area and the die may have a second area, wherein the first area is bigger than the second area. The first area may define a shaft of the probe device and the second area may define an active part of the probe device.

According to embodiments of the invention, the probe device may have a substantially cylindrical shape or a shape with a substantially conical cross-section. An advantage of such shapes is that they do not have sharp edges and therefore minimize damage of the tissue when the probe device is implanted.

In embodiments according to the first aspect of the invention, the device may furthermore comprise a biocompatible insulating coating for protection of the probe against corrosion of contacts present on the substrate and on the die.

In a specific example according to the first aspect of the invention, the probe device may be a neuro-probe device for deep brain stimulation (DBS). The neuro-probe device may comprise:

a substrate having a top surface, and a die positioned on the top surface of the substrate, the die comprising an array of stimulation/recording sites, wherein each stimulation/recording site comprises at least one stimulation means and at least one recording means.

In a second aspect of the present invention, a method is provided for the manufacturing of a probe device according to the first aspect of the invention. The method comprises providing an array of pixels, each pixel comprising at least one stimulation means and at least one recording means. The recording means may be, for example, means that can be used for measuring, indicating, and/or reading the activity of excitable cells present in a tissue to be examined or treated, for example brain tissue.

The method according to the second embodiment of the invention provides a probe device wherein stimulation and recording means are positioned at a same site, forming a stimulation/recording site. Furthermore, because an array of stimulation/recording sites is present, it is possible to stimulate excitable cells and record activity of excited cells in at least two directions.

According to embodiments of the invention the method may furthermore comprise providing the array of pixels on a die.

In further embodiments, the method may furthermore comprise thinning the die comprising the array of pixels. This step may be required in particular when the die is formed of a thick substrate such as Si or GaAs. However, when the die is formed of SOI (silicon on insulator) this step may be omitted because the SOI die may be made thin enough before the start of the manufacturing of the probe device.

The method according to the second embodiment of the invention may furthermore comprise bonding the die comprising the array of pixels onto a substrate.

According to embodiments of the second aspect of the invention, the method may furthermore comprise shaping the substrate so as to enable the probe device, when introduced into tissue of a patient, to perform 3D stimulation of excitable cells present in the tissue and 3D measurement of activity of the excitable cells. In some embodiments, shaping the substrate may comprise folding or bending the substrate. Such shaping the substrate may for example comprise forming a substantially cylindrical device or a device having a shape with a substantially conical cross-section.

In the method according to embodiments of the second aspect of the invention, the die may be bonded onto the substrate by means of wire bonding. In other embodiments, the die may be bonded onto the substrate by means of the flip-chip technique.

According to embodiments of the second aspect of the invention, the method may furthermore comprise providing a biocompatible insulating coating for protection against corrosion of contacts present on the substrate and on the die.

In a specific example of the second aspect of the invention, a method is provided for the manufacturing of a neuro-probe device for performing DBS. The method may comprise:

providing a substrate having a top surface, providing a die comprising an array of stimulation/recording sites, each stimulation/recording site comprising at least one stimulation means and at least one recording means, thinning the die comprising an array of stimulation/recording sites, bonding the die comprising an array of stimulation/recording sites on the top surface of the substrate, and folding the substrate thus forming a device with a cylindrical shape or with a shape having a substantially conical cross-section having an outer side, wherein the folding of the substrate is such that the stimulation/recording sites are at the outside of the cylinder or shape with conical cross-section thus formed.

In a third aspect of the invention, a method is provided for determining a stimulation pattern for application to excitable cells in a tissue using the probe-device according to the invention. The method comprises:

recording electrical activity of excited cells, comparing the recorded electrical activity to predetermined activity values of the excited cells, and from the comparison, determining the stimulation pattern.

The invention also includes a computer program product which, when executed on a processing device, executes the method according to the third aspect of the invention, and a machine readable data storage device storing the computer program product according to the invention.

In a fourth aspect, the present invention provides a device for determining a stimulation pattern for application to excitable cells in a tissue by means of a probe device according to the first embodiment of the present invention. The device comprises:

a probe device according to the first embodiment of the present invention for recording electrical activity of excited cells and generating corresponding activity signals, processing means for comparing the generated activity signals with pre-determined activity signals for the excited cells, and stimulation pattern determining means for generating, from said comparison, stimulation pattern parameters of the stimulation pattern. The stimulation pattern parameters may comprise frequency and/or amplitude and/or pulse duration.

Particular and preferred aspects of the invention are set out in the accompanying independent and dependent claims. Features from the dependent claims may be combined with features of the independent claims and with features of other dependent claims as appropriate and not merely as explicitly set out in the claims.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

BRIEF DESCRIPTION OF THE DRAWINGS

Presently preferred embodiments are described below in conjunction with the appended drawing figures, wherein like reference numerals refer to like elements in the various figures, and wherein.

DETAILED DESCRIPTION

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is, thus, to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

The invention will now be described by a detailed description of several embodiments of the invention. It is clear that other embodiments of the invention can be configured according to the knowledge of persons skilled in the art without departing from the true spirit or technical teaching of the invention, the invention being limited only by the terms of the appended claims.

Excitable cells in tissues (e.g., nervous, cardiac, or muscular tissue) can be modulated or excited by electric fields, in that way providing a possible therapeutic approach for several disorders affecting these tissues.

The present invention provides a probe device which causes only a minimum amount of tissue damage when it is inserted, which can perform measurements in three dimensions and which has a low electrode impedance and, thus, a low power consumption. The present invention also provides a method for the manufacturing of such a probe device. The probe device will mainly be described by means of a neuro-probe device suitable for use in deep brain stimulation (DBS). It has, however, to be understood that this is not limiting the invention and that the probe device according to the invention may also be used for other applications, such as stimulation of muscles.

The probe device for stimulation and recording of electrical cell activity according to the invention may be used for the treatment of movement disorders, like essential tremor and dystonia, the treatment of chronic neuropathic pain, the treatment of epilepsy and the treatment of psychiatric disorders, like obsessive-compulsive disorder and major depression disorder. Within the nervous system, applications include the motor cortex stimulation for the treatment of tinnitus, and the spinal cord and peripheral nerve stimulation. Outside the nervous system, this technology may become useful in EMG, cardiac pacing and uro-abdominal applications.

Functional electrical stimulation represents a means of producing, by means of electrical stimulation, contractions in muscles which are paralyzed due to lesions of the central nervous system. Applications are found in stroke, spinal cord injury, head injury, cerebral palsy and multiple sclerosis.

When, in the description and in the claims, the term "recording means" is used, a means is meant which can be used for measuring, indicating, and/or reading the cell activity of excitable cells present in the tissue to be examined or treated, such as brain tissue in case of deep brain stimulation (DBS).

Figure 6:
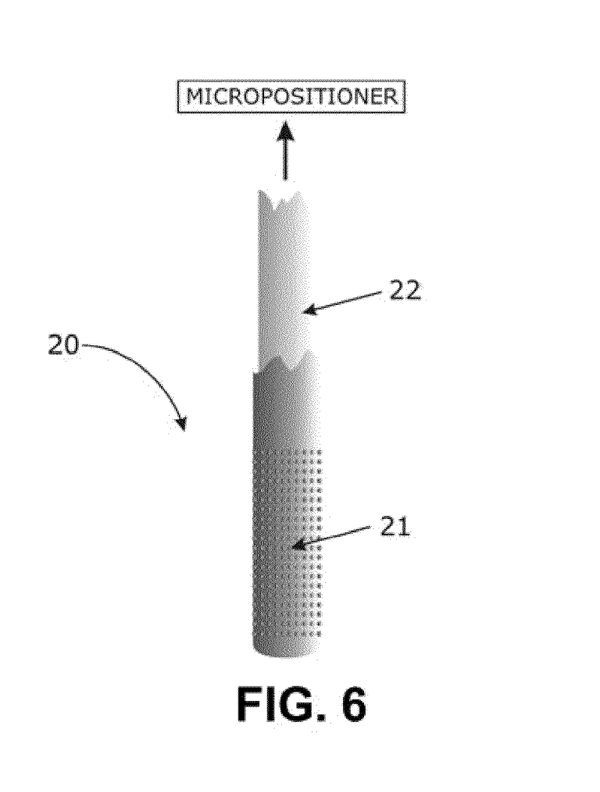
FIG. 6 is a 3D view of a probe according to embodiments of the present invention.

In a first aspect of the invention, a probe device, for example, a neuro-probe device, is provided. FIG. 6 illustrates such a probe device 20 according to this first aspect. The probe device 20 comprises a micro-fabricated array formed by a plurality of pixels 21 forming stimulation/recording sites. The array may be formed by n rows by m columns of pixels 21; the rows and columns of pixels being located on a substantially cylindrical surface.

Furthermore, the terms "column" and "row" are used to describe sets of array elements which are linked together. The linking can be in the form of a Cartesian array of rows and columns; however, the present invention is not limited thereto. As will be understood by those skilled in the art, columns and rows can be easily interchanged and it is intended in this disclosure that these terms be interchangeable. Also, non-Cartesian arrays may be constructed and are included within the scope of the invention. Accordingly the terms "row" and "column" should be interpreted widely. To facilitate in this wide interpretation, there may be referred to "logically organized rows and columns". By this is meant that sets of memory elements are linked together in a topologically linear intersecting manner; however, that the physical or topographical arrangement need not be so.

The surfaces of the probe device 20, e.g., a neuro-probe device, that are in contact with the tissue, such as brain tissue in case of a neuro-probe device used for DBS, are fabricated from or coated with biocompatible materials. The surfaces which are in contact with the brain are the stimulation/recording sites 21 which may be fabricated from noble metals, such as Au, Pt or Ir, and the insulating coating, which may be formed of oxides (e.g., IrOx, $Ta_2O_5$, $SiO_2$, $ZrO_2$), $Si_3N_4$, polymers (e.g., parylene C, parylene N, silicone rubbers, polyimides), or biocompatible epoxies.

Each pixel 21 comprises at least one stimulation transducer or micro-electrode for stimulating a part of the tissue, for example brain tissue in the case of DBS, and at least one recording transducer or micro-electrode for measuring activity of a part of the tissue. Each pixel 21, thus, comprises at least two micro-electrodes. In the further description, the pixels 21 will be referred to as stimulation/recording sites 21.

The at least one stimulation transducer present in each stimulation/recording site 21 is formed by a microelectrode which may comprise a noble metal (e.g., Au, Pt, Ir). Preferably, Pt and/or Ir may be used for the delivery of the stimulation pulses when in contact with excitable cells, such as neurons in case of DBS. The microelectrodes should be able to deliver monophasic cathodic or biphasic pulses generated by a voltage controlled pulse generator (0 to 20 V stimulus amplitude, 20 to 1000 μsec, for example between 60 and 200

μsec pulse duration and 2 to 1000 Hz, for example between 60 and 200 Hz frequency). For the treatment of, for example, obsessive-compulsive disorders rather high pulse durations may be required. For the treatment of, for example, chronic pain lower frequencies, such as 20 Hz, may be required. In embodiments according to the invention, also a constant current pulse generator may be used for generating pulses.

Field-effect transistors (FETs) may, for example, be used as recording transducers or micro-electrodes for recording of the cell activity. The signal provided by the recording transducers may be further processed by a controller, e.g., a microprocessor unit, which may be placed somewhere on the dura mater in a burr hole or below the skin. This unit may also provide a required pulse pattern to be applied to the stimulation electrodes. The steering electronics can be completely external to the tissue, e.g., brain in case of DBS; or may be distributed between the probe device 20, e.g., neuro-probe device in case of DBS, and an external part thereof. Although the term 'external' is used, this does not mean that the steering electronics are necessarily outside the body of the patient. In case of DBS, this also includes that the steering electronics may be implanted not in the brain itself, but between the skull and the dura mater in a burr hole or below the skin.

Each stimulation/recording site 21 may have a width and length between 5 and 100 μm. Preferably, each pixel or stimulation/recording site 21 may have a size of between 5 and 50 μm, more preferably between 5 and 30 μm, and most preferably between 5 and 10 μm. The size of the stimulation/recording sites 21 determines the resolution of the probe device 20, e.g., neuro-probe device. Therefore, in order to obtain a good resolution, each stimulation/recording site 21 may preferably be as small as possible because the better the resolution is, the more precise the controllability of the probe device 20 becomes. However, the smaller the surface area of the stimulation electrode, the higher the charge density will become ($\mu Coul/cm^2$). The charge density determines the amount of current that can be delivered, and this should happen without damaging the tissue where the probe device 20 is positioned, e.g., the brain in case of DBS.

The array comprising the stimulation/recording sites 21 may be a CMOS array, and is bonded to a biocompatible substrate, also called packaging substrate, with a given geometry suitable for implantation in the relevant anatomic target (e.g., STN). According to the invention, 3D field distribution is important and the geometry of the probe device 20 should enable this. Therefore, ideally, the probe device 20, and therefore the substrate thereof, may have a substantially cylindrical shape or may have a conical cross-section with the active pixels or stimulation/recording sites 21 distributed on the external site and, thus, in contact with the tissue, such as brain tissue.

Due to the stimulation transducers and recording transducers of the pixels 21 being located in an array, this array being bonded onto a substrate having a substantially cylindrical shape or a shape with a conical cross-section, the electrical field distribution can be controlled. Furthermore, recordings of electrical activity of excitable cells (such as neuronal electrical activity in case the probe device 20 is a neuro-probe device for performing DBS) can be performed in three dimensions.

The probe device 20 according to the invention has no sharp edges and in that way damage to the tissue, for example brain, such as hemorrhage, is avoided. Furthermore, the probe device 20 has a sufficient flexibility for optimal conformity to the tissue target, e.g. brain target. This may be achieved by folding or bending the flexible packaging substrate. Once the stimulation/recording sites 21 are bonded to the substrate, the flexible substrate comprising the attached array of stimulation/recording sites 21, e.g., deep brain stimulation and recording or DBSR array, will be folded or rolled around a micro-catheter 22 which is used for implantation of the probe device 20 into the tissue, such as brain tissue.

Because the probe device 20 according to the invention, due to its shape and the distribution of a large number of stimulation/recording sites thereon, has the possibility to perform measurements in three dimensions, the probe device 20 can work with high spatial resolution and high signal-to-noise ratio. Furthermore, with the probe device 20 according to the present invention, recordings of the activity of excitable cells, for example, cellular activity in the STN, could be used for providing feedback, allowing the stimulation only while necessary, leading to a substantial power consumption saving. Moreover, the probe device 20 according to the first aspect of the invention is able to perform electrical stimulation and recording of the activity of excitable cells, for example deep brain stimulation and recording, at single cell level which makes it possible to understand the mechanisms responsible for the therapeutic effect of the technique.

Furthermore, the probe device 20 according to the invention can also correct for movement of the tissue. The tissue may be moving and it is not unusual for a probe device, in particular for a neuro-probe device, to be displaced. Movement of the probe device 20 can lead to a recording pattern indicating loss of therapeutic effect, as a surgeon knows the correct pattern of cell activity for certain excitable cells and that pattern is then compared to the pattern that is recorded. Because of displacement, this recorded pattern can be incorrect and thus can give errors when used for determining therapeutic effects. By means of steering electronics, specific stimulation/recording sites 21 can be controlled allowing reconfiguration of the stimulation pattern. When the probe device 20 has moved, this may be detected by the recordings. When moving of the probe device 20 is observed, other stimulation/recording sites can be addressed for obtaining the required signal.

According to the present invention, the small recording electrodes are incorporated along the probe shaft. Therefore, cell activity can be measured in the near vicinity of each stimulation site, and not only at the tip as is the case in the device described in U.S. Patent Publication No. 2002/0022872. In this way, correction of the stimulation signal to be applied at a given location and thus compensation for vertical and lateral movement can be performed. The recording electrode is an active device, such as a transistor, generating local signal amplification and high to low impedance conversion.

The device 20 according to the present invention may be used in surgical Parkinson's Disease therapy, but is also suitable for modulation of excitable cells in the treatment of other disorders such as other movement disorders (essential tremor, posttraumatic tremor, tremor in multiple sclerosis, dystonia), epilepsy, chronic pain (chronic neuropathic and non-neuropathic pain, cluster headache, and so on), obesity, arterial hypertension, tinnitus, psychiatric disorders (e.g., obsessive-compulsive disorders, depression, anxiety, anorexia nervosa, and so on).

It has to be remarked that the probe device 20 according to the invention is compatible with existing signal processing and control circuitry and implant positioning procedures.

Figure 7:
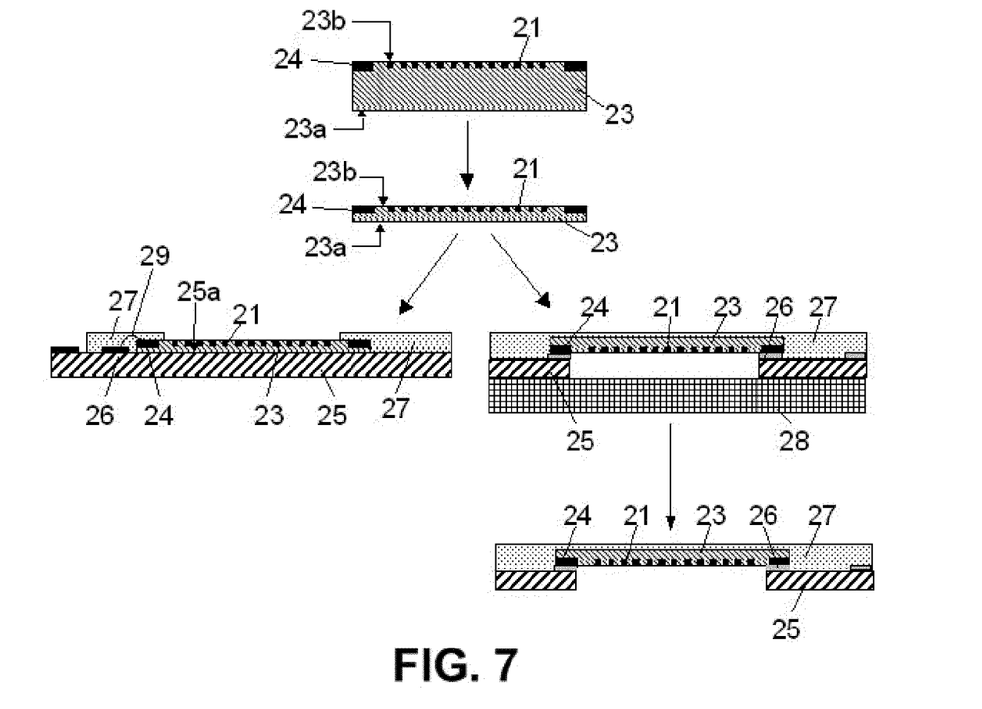
FIG. 7 illustrates two possible packaging methods, i.e., wire bonding approach (left) and flip chip approach (right), for use with a probe according to the present invention.

In a second aspect of the invention, a method for the manufacturing of a probe device 20 according to the first aspect of the invention will be discussed and illustrated in FIG. 7. The method will merely be described for a neuro-probe device 20, which may be used for deep brain stimulation. However, it is to be understood that this example is not limiting and that other probe devices 20, such as probe devices 20 to be implanted in muscular tissue or cardiac tissue for stimulating excitable cells within these tissues may also be manufactured using the method according to the invention.

In a first step, an array of stimulation/recording sites 21 is formed on a die 23, which may, for example, be a silicon die. Hereinafter, the method for the manufacturing of a probe device 20 according to the first aspect of the invention will be described for a silicon die 23. It has to be understood that this is not a limiting example and that other semiconductor materials, such as GaAs and SOI, can also be used. However, in the case of SOI, the method may be adapted in the sense that no thinning step may be needed as SOI can be made thin enough before the start of the manufacturing of the probe device 20.

Formation of the stimulation/recording sites 21 onto the die 23 may be performed by means of micro-fabrication techniques known by persons skilled in the art, such as, for example, IC or CMOS standard and non-standard processes. The die 23 may have a thickness of between 300 μm and 1 mm, for example 850 μm.

It is an advantage of the present invention that the array of stimulation/recording sites 21 may be applied by a standard process on a standard substrate, as this makes the fabrication process easier than making the array of stimulating/recording sites directly on a substantially cylindrical or conical substrate. Contacts 24 are provided using, for example, standard CMOS metallization processes. Suitable materials for forming the contacts 25 may, for example, be Al or Au or any other suitable noble metal.

In a next step, the die 23 on which the array of stimulation/recording sites 21 is formed may first be thinned down to, for example, 50 μm, preferably down to 25 μm, more preferably down to 10 μm, and most preferably down to 5 μm. As already discussed, in case the die is formed of SOI, this thinning step may not be necessary because the SOI die may already be thin enough.

In the case that the probe device 20 only comprises passive electrodes, e.g., metal lines, it could be processed on all kind of substrates including plastic. However, the signal to noise ratio and, thus, the chronic recording will be poor with such electrodes. Also thin-film transistors have poorer properties compared to silicon transistors. Therefore, preferably standard CMOS processing performed on semiconductor substrates, such as Si, GaAs or SOI substrates, may be used according to embodiments of the present invention. Thinning down is performed down to a thickness of the die low enough to make the die flexible. Thinning down may be performed by any suitable method, such as mechanical and/or chemical polishing.

In a next step, the thinned die 23 comprising the stimulation/recording sites 21 is bonded to a substrate 25. The substrate 25 may, for example, comprise biocompatible material such as any of parylene C, parylene N, polyimide, polysiloxane rubber or teflon, but may also comprise a noble metal (e.g. Au, Pt, Ir), titanium, oxides (e.g. IrOx, $Ta_2O_5$, $SiO_2$, $ZrO_2$), $Si_3N_4$ or biocompatible epoxies. The material the substrate 25 is formed of should be such that cytotoxicity and material degradation is prevented when the probe device 20 is implanted in the tissue, for example, the brain in case of a neuro-probe device 20 for DBS.

The substrate 25 has an area and lies in a plane, the area extending in the direction of its plane. The die 23 comprising the stimulation/recording sites 21 also has an area, the area of the die 23 extending in a direction substantially parallel to the plane of the substrate 25. The area of the substrate 25 may preferably be larger than the area of the die 23 comprising the stimulation/recording sites 21. The die 23 comprising the stimulation/recording sites 21 forms the active part of the probe device 20. The substrate 25 represents a probe shaft and it may be used to anchor the probe device 20 on the dura mater in a burr hole or below the skin.

The packaging or bonding method may be based on either wire bonding or flip chip assembly of the die 23 comprising the array of stimulation/recording sites 21 onto the substrate 25, which is a biocompatible flexible substrate that can subsequently be folded to acquire a desired shape, preferably a tubular or conical shape. The process flows for the wire bonding approach (left hand side) and for the flip chip approach (right hand side) are both schematically illustrated in FIG. 7.

In the wire bonding approach, the die 23 comprising the array of stimulation/recording sites 21 is positioned with its bottom surface 23a to the top surface 25a of the substrate 25, and its contacts 24 are wire bonded, i.e., connected with fine metal wires, such as gold wires, to contacts 26 present at the substrate 25, as known by persons skilled in the art. The contacts 24 on the die 23 and the contacts 26 on the substrate 25 are then covered by a biocompatible insulating coating 27. The biocompatible insulating coating 27 may for example be oxides (e.g., IrOx, $Ta_2O_5$, $SiO_2$, $ZrO_2$), $Si_3N_4$, polymers (e.g., parylene C, parylene N, silicone rubbers, polyimide) or biocompatible epoxies. This biocompatible insulating coating 27 is required for passivation reasons. Only the 'active area' of the stimulation/recording sites 21 should be allowed to be in contact with the brain. The rest of the probe device 20, mainly the electrical connections, are in that way protected to avoid corrosion or other undesirable reactions between the material in which they are made and the brain.

In the flip chip approach (right hand side of FIG. 7), a patterned flexible substrate 25 is provided onto a sacrificial substrate 28. The sacrificial substrate 28 may comprise any suitable material such as silicon, plastics (e.g. polycarbonates, polyethersulphone, polyimides) or glass. Suitable materials should be sufficiently strong and be able to form planar surfaces. Contacts 26 are provided on the top surface 25a of the substrate 25.

The die 23 comprising the stimulation/recording sites 21 is then bonded to the top surface 25a of the substrate 25 such that the contacts 24 on the die 23 match the contacts 26 on the top surface 25a of the substrate 25. Optionally, a sacrificial layer (not shown) may be present between the sacrificial substrate 28 and the flexible substrate 25. The sacrificial layer may be, for example, a thin metal layer (e.g., Al, Au), a polymer, an acetone soluble wax or a self-assembled monolayer of molecules that prevent strong adhesion (e.g., silanes, thiols, fluoropolymers). A biocompatible insulating coating 27 is then provided over the die 23 and over the flexible substrate 25. The biocompatible insulating coating 27 may for example be oxides (e.g. IrOx, $Ta_2O_5$, $SiO_2$, $ZrO_2$), $Si_3N_4$, polymers (e.g., parylene C, parylene N, silicone rubbers, polyimide) or biocompatible epoxies.

After that, the sacrificial substrate 28 is removed. This may be performed by peeling off the flexible substrate 25. In other embodiments, in case a sacrificial layer was present between the sacrificial substrate 28 and the flexible substrate 25, removing the sacrificial substrate 28 may be performed by removing this sacrificial layer by dissolution in its own solvent. For example, if the sacrificial layer is a solvent-soluble polymer it will dissolve in the given solvent, for example, acetone-soluble wax can be removed by immersing in acetone.

Figure 8:
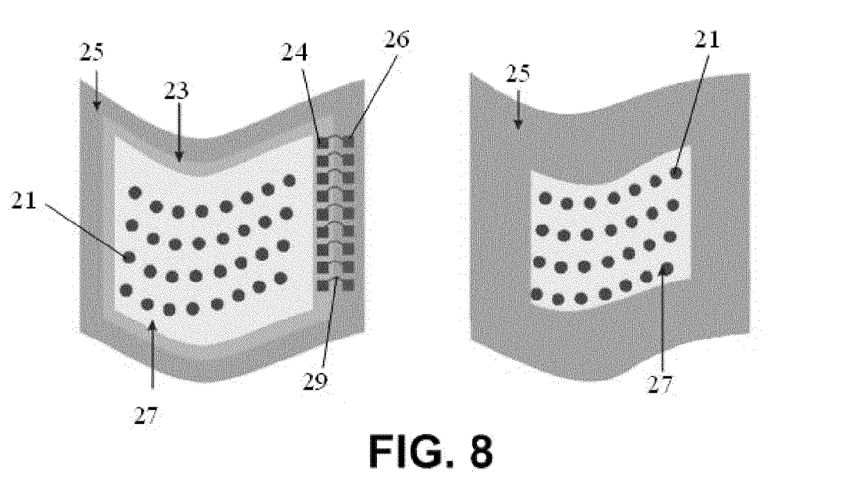
FIG. 8 is a side view of the flexible substrate with the attached probe device chip wire bonded (left) or flip-chipped (right) according to embodiments of the present invention.

FIG. 8 illustrates the die 23 bonded onto the flexible substrate 25. At the left hand side of FIG. 8, the result of the wire bonding approach is shown. This figure clearly shows the fine wires 29 between the contacts 24 on the die 23 and the contacts 26 on the flexible substrate 25. At the right hand side of FIG. 8 the result of the flip chip approach is shown.

In a next step, the substrate 25 is shaped, for example, folded or bent around a rigid catheter 22 (see FIG. 6) that may then be used for insertion of the probe device 20 in the tissue, e.g. brain, and which is removed after the implantation procedure is performed. The structure may fold or bend by itself due to internal stress in the sheet, i.e., a sort of curling or a lamination method could be used. Once folded, the sides of the probe device 20 are attached to each other, so as to form a substantially cylindrical shape or a shape having a conical cross-section. This may be done by any suitable attaching means, such as gluing of the sides onto each other, which may be thermally induced (local heating) or may be performed by using biocompatible glues, such as UV curable epoxies or silicones.

It has to be understood that the step of shaping, such as folding or bending, is not always required. The probe device may also be implanted in the tissue to be treated as a two dimensional array of pixels, each pixel comprising a stimulation and a recording means. In this case, the step of attaching sides to each other may not be necessary either.

An advantage of the method according to the second aspect of the invention is that it provides a probe device that does not have sharp edges. Hence, when implanting the probe device 20, damage to the tissue, e.g. brain tissue in case of a neuro-probe device 20 used for DBS, can be minimized. Furthermore, the method according to the second aspect of the invention allows for the required electronics to be easily incorporated into the probe device 20.

Figure 9:
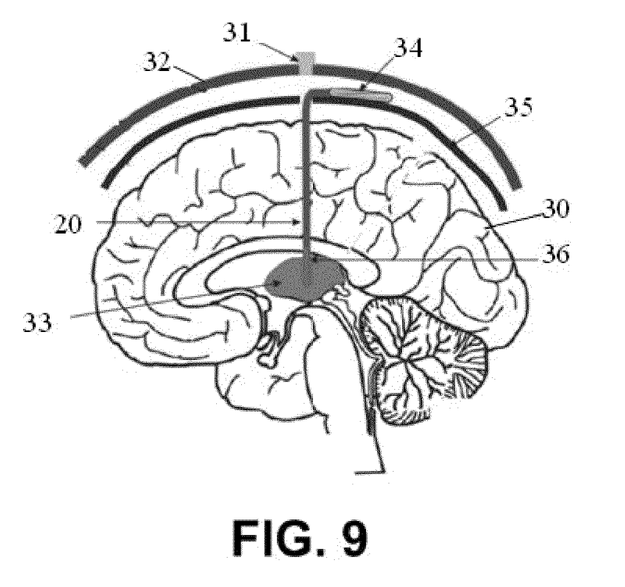
FIG. 9 illustrates a neuro-probe according to an embodiment of the present invention implanted in the subthalamic nucleus.

FIG. 9 illustrates the specific example of a neuro-probe device 20 implanted in the brain 30 of a patient. The neuro-probe device 20 may be implanted with existing and known implant procedures and methods. An insertion zone 31 is provided in the skull 32 of the patient. The neuro-probe device 20 is implanted through the insertion zone 31 such that part of the neuro-probe device 20 is positioned in the thalamus 33. Processing means, such as control electronics 34 may be positioned externally to the brain, for example, between the skull 32 and the dura mater 35, and fixed to the dura mater 35.

The length of the implanted neuro-probe device 20 may be in the range of between 2 and 50 mm, preferably, the length of the neuro-probe device may be between 2 and 9.5 mm, and most preferably the length to the neuro-probe device 20 may be between 2 and 5 mm. The diameter of the neuro-probe device 20 may be between 100 μm and 1 mm. A rigid stylet can be used to control the position of the device during the implantation procedure, which may then be removed when the neuro-probe device 20 is successfully implanted. The active part 36 of the neuro-probe device 20 is formed by the die 23 comprising the stimulation/recording sites 21. The part of the substrate 25 that is not covered by the die 23 with the stimulation/recording sites 21 forms the shaft of the neuro-probe device 20 and may be used to anchor the neuro-probe device 20 onto the dura mater 35.

Already during the insertion of the neuro-probe device 20 in the brain, or more in general, during insertion of the probe device 20 in tissue, the microelectrodes will record electrical activity of neighboring cells. These recorded signals will be further amplified and processed in a processing means or control unit, such as in microprocessor 34, allowing to clearly define the limits of the anatomic target, i.e., the tissue to be treated or examined, in the example given the brain tissue.

It may be possible to implant one or more neuro-probe devices 20, one next to the other, in order to account for lateral deviation of the neuro-probe device 20 in relation to the target, i.e., the tissue to be treated or examined, in the example given the brain tissue. The signals may be recorded during surgery under local or general anaesthesia, or even days or years after surgery, either with the patient at rest or during performance of a certain activity, e.g., the patient lifting the arm versus the patient not moving the arms, or during application of a stimulus to the patient, e.g., during the moment the clinician touches the arm with a brush versus without touching, or during certain conditions of the patient, e.g., during akinesia versus during a period without akinesia. By doing so, it may become clear that certain recording microelectrodes produce signals in relation to the activity of the patient or the stimulus which has been applied to the patient.

Hereinafter the example of akinesia will be described in order to make the above-described method more clear. During akinesia, which is a symptom of Parkinson's disease, the recorded signals may be different from the ones when there is no akinesia. This information could later-on be used to produce feedback to stimulating microelectrodes that reduce the akinesia. The stimulator may be made active during the period of akinesia and inactive during the period of well-being. This feedback system may diminish side-effects of stimulation and may also prolong battery life of the stimulator.

Hence, pulse trains of 'therapeutic' stimuli with different amplitude, duration, and/or frequency may be applied and the cellular activity may be recorded before, during and after stimulation. The processing means, e.g., microcontroller or microprocessor 34, may analyze the characteristics of the signals recorded before, during, and after applying a stimulation pulse at different locations on the neuro-probe device 20, compare these signals with pre-determined signals, and define the most effective pattern for the stimulation, i.e., which pixels should be addressed for stimulation at which time intervals and with which stimulus parameters. This stimulation pattern may then be used during further therapy. During post-operation check-ups the neurosurgeon may have the opportunity to control if the efficacy of the stimulation is maintained. This may be done by controlling the activity recordings corresponding with stimulation patterns and, if necessary, amending the stimulation pattern.

The present invention furthermore includes a computer program product that provides, when executed on a computing device, the functionality of the method for determining a stimulation pattern for application to excitable cells in a tissue, using a probe-device 20 according to embodiments of the present invention. Further, the present invention includes a data carrier such as a CD-ROM or a diskette, which stores the computer program product of the present invention in a machine readable form and which executes the method for determining a stimulation pattern for application to excitable cells in a tissue using a probe-device 20 according to embodiments of the present invention when executed on a computing device. Nowadays, such software is often offered on the Internet or a company Intranet, e.g., a hospital internet, for download, hence the present invention includes transmitting the stimulation pattern determining computer product according to the present invention over a local or wide area network. The computing device may include one of a microprocessor and an FPGA.

The present invention furthermore provides a device for determining a stimulation pattern for application to excitable cells in a tissue by means of a probe device according to the first embodiment of the present invention. The device comprises:

a probe device according to the first embodiment of the present invention for recording electrical activity of excited cells and generating corresponding activity signals, processing means for comparing the generated activity signals with pre-determined activity signals for the excited cells, and stimulation pattern determining means for generating, from said comparison, stimulation pattern parameters of the stimulation pattern. The stimulation pattern parameters may comprise frequency, amplitude, and/or pulse duration.

It is to be understood that although preferred embodiments, specific constructions and configurations, as well as materials, have been discussed herein for devices according to the present invention, various changes or modifications in form and detail may be made without departing from the scope and spirit of this invention. The claims should not be read as limited to the described order or elements unless stated to that effect. Therefore, all embodiments that come within the scope and spirit of the following claims and equivalents thereto are claimed as the invention.

We claim:

1. A probe device for electrical stimulation and recording of activity of excitable cells in brain tissue, the probe device comprising:
    a flexible substrate having a first area and comprising an exterior planar surface, wherein the flexible substrate is shaped to minimize brain tissue damage;
    a semiconductor die having a second area smaller than the first area and positioned on the exterior planar surface; and
    an array of pixels formed on the semiconductor die, wherein each pixel comprises at least one stimulation means and at least one recording means.

2. The probe device of claim 1, wherein the probe device has one of a substantially cylindrical shape and a shape with a substantially conical cross-section.

3. The probe device of claim 1, wherein the first area defines a shaft of the probe device and the second area defines an active part of the probe device.

4. The probe device of claim 1, wherein the die is a silicon die.

5. The probe device of claim 1, wherein the substrate comprises one of parylene C, parylene N, polyimide, polysiloxane rubber, teflon, a noble metal, titanium, an oxide, $Si_3N_4$, and biocompatible epoxies.

6. The probe device of claim 1, further comprising a biocompatible insulating coating for protection against corrosion of contacts present on the substrate and on the die.

7. The probe device of claim 1, wherein the probe device is a neuro-probe device for performing deep brain stimulation.

8. A method for the manufacturing of a probe device for electrical stimulation and recording of activity of excitable cells in brain tissue, the method comprising:
    providing a die comprising an array of pixels, wherein the die comprises a semiconductor material, and each pixel comprises at least one stimulation means and at least one recording means;
    thinning the die comprising the array of pixels;
    providing a flexible substrate comprising an exterior planar surface;
    bonding the die comprising the array of pixels onto the exterior planar surface, wherein the substrate has a first area, the die has a second area, and the first area is bigger than the second area; and
    shaping the flexible substrate in a manner to minimize damage of the brain tissue when the probe device is implanted.

9. The method of claim 8, wherein shaping the substrate includes at least one of folding the substrate and bending the substrate.

10. The method of claim 9, wherein shaping the substrate comprises forming a device with at least one of a substantially cylindrical shape and a shape having a substantially conical cross-section.

11. The method of claim 8, wherein bonding the die on the substrate is performed by means of wire bonding.

12. The method of claim 8, wherein bonding the die on the substrate is performed by means of the flip chip technique.

13. The method of claim 8, further comprising providing a biocompatible insulating coating for protection against corrosion of contacts present on the substrate and on the die.

14. A method for determining a stimulation pattern for application to excitable cells in brain tissue, the method comprising:
    providing a probe device comprising:
        a flexible substrate having a first area and comprising an exterior planar surface, wherein the flexible substrate is shaped to minimize brain tissue damage;
        a semiconductor die having a second area smaller than the first area and positioned on the exterior planar surface; and
        an array of pixels formed on the semiconductor die, wherein each pixel comprises at least one stimulation means and at least one recording means;
    using the probe device to record electrical activity of excited cells;
    making a comparison of the recorded electrical activity to predetermined activity values of the excited cells; and
    based on the comparison, determining the stimulation pattern.

15. A computer program product stored on a non-transitory computer-readable medium which when executed on a processing device executes the method of claim 14.

16. A device for determining a stimulation pattern for application to excitable cells in brain tissue, the device comprising:
    a probe device for recording electrical activity of excited cells and generating corresponding activity signals, the probe device comprising:
        a flexible substrate having a first area and comprising an exterior planar surface, wherein the flexible substrate is shaped to minimize brain tissue damage;
        a semiconductor die having a second area smaller than the first area and positioned on the exterior planar surface; and
        an array of pixels formed on the semiconductor die, wherein each pixel comprises at least one stimulation means and at least one recording means;
    processing means for making a comparison of the generated activity signals with pre-determined activity signals for the excited cells; and
    stimulation pattern determining means for generating, from said comparison, stimulation pattern parameters of the stimulation pattern.

17. The device of claim 16, wherein the stimulation pattern parameters are selected from the group consisting of frequency, amplitude, and pulse duration.

* * * * *